United States Patent [19]

Ryan

[11] Plant 4,364

[45] Jan. 2, 1979

[54] IMPATIENS PLANT SHAWNEE

[76] Inventor: John J. Ryan, 39877 Sundale Dr., Fremont, Calif. 94538

[21] Appl. No.: 874,930

[22] Filed: Feb. 3, 1978

[51] Int. Cl.[2] ..... A01H 5/00

[52] U.S. Cl. ..... Plt./68

[58] Field of Search ..... Plt./68

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Shawnee, and discovered by me in commercial greenhouses in Fremont, Calif.

If pressed to compare to a known variety, Shawnee has a foliage that is closest in comparison to U.S. Department of Agriculture Arabesque; but the comparison is slight. Shawnee is unlike other varieties because of its distinctively wide variegation (dark green outer rim with prominent red veins in an off-gold center), its upright growth habit, good breaking action, fairly compact, and a medium-sized pink flower.

1 Drawing Figure

BACKGROUND OF THE INVENTION

The present new variety (seedling) was discovered by me in a commercial greenhouse in Fremont, Calif. as a result of the cross pollination of the pistil parent 76-36-10 (Navajo) for which a U.S. application, Ser. No. 782,285 was filed 3-28-77, now U.S. Plant Pat. No. 4,259, and the unpatented pollen parent 75-38.

Asexual reproduction of my new cultivar by terminal or stem cuttings grown in pots in a plastic (polyethylene) greenhouse in Fremont, Calif. under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Shawnee is closest in characteristics to U.S. Department of Agriculture Arabesque, but the comparison is only slight. The following outstanding characteristics of Shawnee distinguish it from U.S. Department of Agriculture Arabesque:

1. Much more floriferous.
2. A smaller medium pink flower compared to U.S. Department of Agriculture Arabesque's very large white flower with candy stripes.
3. Leaf size is smaller.
4. Variegation is more distinct with dark green and more reddening in veins.
5. Growth habit more upright with better breaking action.

DESCRIPTION OF THE PHOTOGRAPH

The accompanying colored photograph illustrates the overall appearance of the cultivar Shawnee showing the colors as true as reasonably possible for this type of colored reproduction. Although high light and temperature increases variegation width and lightens flower color, Shawnee doesn't show the degree of change some other varieties do.

DETAILED DESCRIPTION

The following detailed description of Shawnee was based on observations made of the new cultivar on Nov. 15, 1977.

I. Plant

Name: Shawnee.
Origin: Seedling of the cross pollination of pistil parent 76-36-10 (Navajo) U.S. patent application, Ser. No. 782,285 filed 3-28-77 and unpatented pollen parent 75-38.
Form: Upright.
Height to flowering: 30 cm. to 38 cm.
Growth: Moderate.
Type of cutting: Terminal or stem.
Rooting time: Typical, 10–14 days.
Rooting habit: Fast, dendritic.

II. Foliage

Arrangement: Lower leaves of any break are opposite; upper foliage of any break are whorls of 3 to 5.
Shape: Older leaves are generally oblanceolate, newer leaves are elliptical to lanceolate.
Tip: Acuminate.
Base: Attenuate.
Margin: Serrulate.
Venation: Pinnate.
Size: Blade and petiole 8 cm. to 11.5 cm.; length of blade 6 cm. to 9 cm.; width at widest point 2.5 cm. to 3.5 cm.
Surface: Glabrous, glossy.
Variegation: High light and age of cutting increase variegation; whereas low light and high fertilization reduce variegation and increase leaf size.
Color:

1. *Petiole.*—52 A to 52 B.
2. *Veins.*—52 A to 52 B.
3. *Leaf.*—a. Upper: Exposed to light at top of plant 147 A, lower leaves shaded 137 A. b. Lower: 184 A.
4. *Variegation.*—a. Edge 19 B grades into 147 A. b. Middle 19 B. c. Center 19 B.

III. Stem

Color: 52 C.
Internode:
1. *Length.*—Moderate.
2. *Size.*—Moderate.

Node expanded (relative to internode): Slightly expanded.
Breaking action: Good.

IV. Flower

Form: Typical.
Borne: End of branches, terminal.
Blooming habit:
1. *Relative number.*—Average.
2. *Time to flowering.*—Average.
3. *Longevity.*—Typical, 3–5 days.

Size of mature flower: First flower on a plant may be small.
1. *Length.*—4.5 cm. to 5.5 cm.
2. *Width.*—4.5 cm. to 5.0 cm.
3. *Spur.*—5.0 cm. to 5.5 cm.

Color: Lighter pink under high light and heat.
1. *Eye.*—68 B to 68 C
2. *Middle* } 52A to 52 B to 55 C because candy stripes and some inner edges are darker.
3. *Edge* }
4. *Pedicel.* —10 D.

V. Reproductive organs

Stamen:
1. *Anthers* } Typical, fused hood over pistil, but smaller than average
2. *Filaments* }
3. *Pollen.*—a. Color: 11 C. b. Abundance: Less than average.

Pistils:
1. *Style* } Typical, but small
2. *Ovaries* }

VI. Other characteristics

Shawnee shows good resistance to soft rots and spider mites.

Shawnee has a more upright leaf habit, which is demonstrated in the photograph by the showing of the underside of many leaves.

I claim:

1. A new and distinct form of Impatiens plant as described and illustrated, known by the cultivar name Shawnee, and particularly characterized by its distinctively wide variegation (dark green outer rim with prominent red veins in an off-gold center); its upright growth habit; good breaking action; fairly compact; and a medium pink flower.

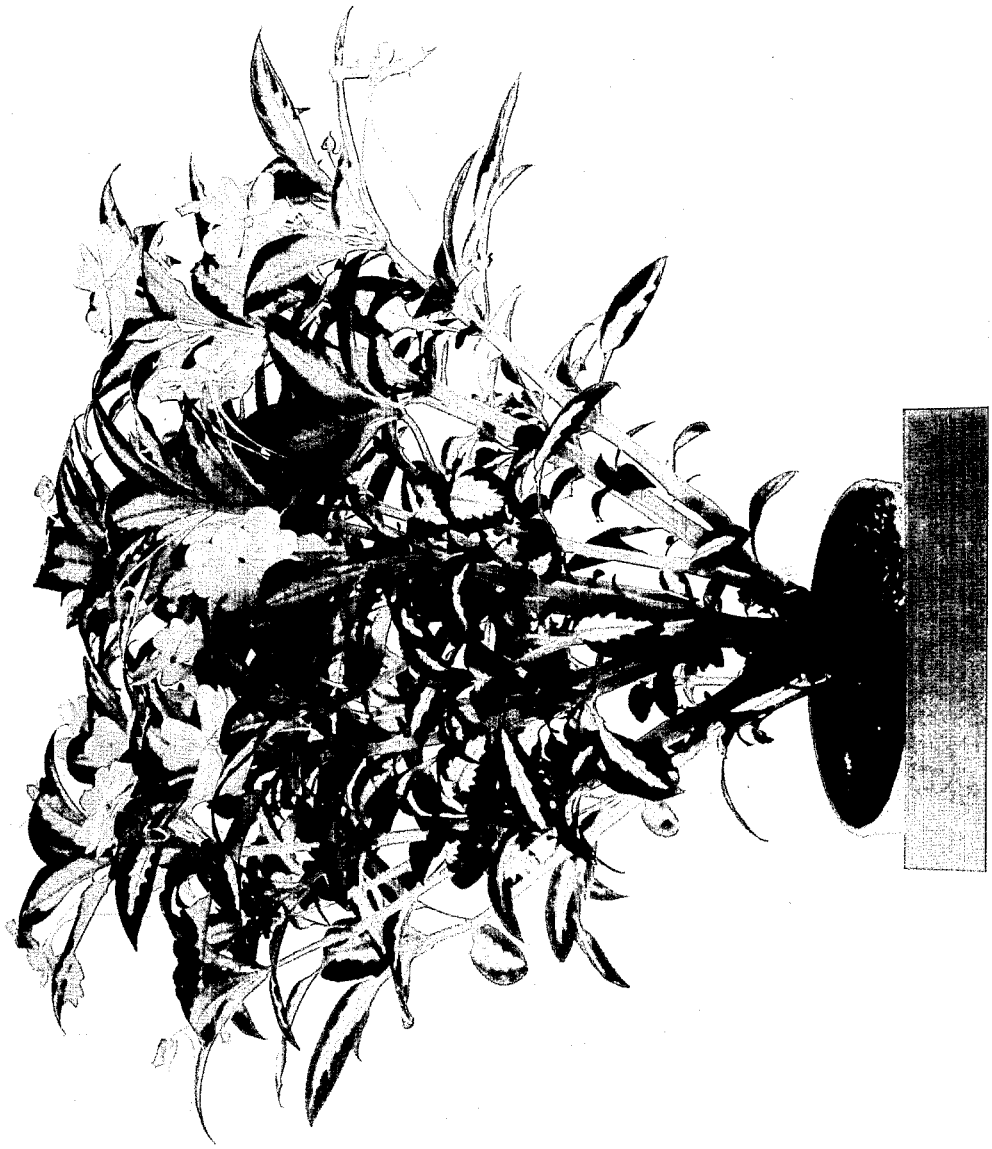

* * * * *